(12) United States Patent
Kramer et al.

(10) Patent No.: US 7,158,828 B2
(45) Date of Patent: Jan. 2, 2007

(54) SYSTEM AND METHOD FOR TIMING SYNCHRONIZED PACING

(75) Inventors: Andrew P. Kramer, Stillwater, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 596 days.

(21) Appl. No.: 10/454,014

(22) Filed: Jun. 3, 2003

(65) Prior Publication Data

US 2003/0195575 A1 Oct. 16, 2003

Related U.S. Application Data

(63) Continuation of application No. 09/748,736, filed on Dec. 26, 2000, now Pat. No. 6,574,506.

(51) Int. Cl.
*A61N 1/368* (2006.01)
(52) U.S. Cl. .............. 607/9; 607/15; 607/148
(58) Field of Classification Search ............. 607/9, 607/15, 148
See application file for complete search history.

(56) References Cited

U.S. PATENT DOCUMENTS

| 4,354,497 A | 10/1982 | Kahn | 128/419 D |
|---|---|---|---|
| 4,928,688 A | 5/1990 | Mower | 128/419 PG |
| 5,156,149 A | 10/1992 | Hudrlik | 128/419 PG |
| 5,174,289 A | 12/1992 | Cohen | 128/419 PG |
| 5,233,985 A | 8/1993 | Hudrlik | 607/27 |
| 5,267,560 A | 12/1993 | Cohen | 607/25 |
| 5,370,665 A | 12/1994 | Hudrlik | 607/9 |
| 5,514,161 A | 5/1996 | Limousin | 607/9 |
| 5,584,867 A | 12/1996 | Limousin et al. | 607/9 |
| 5,674,259 A | 10/1997 | Gray | 607/20 |
| 5,797,970 A | 8/1998 | Pouvreau | 607/9 |
| 5,902,324 A | 5/1999 | Thompson et al. | 607/9 |
| 5,935,160 A | 8/1999 | Auricchio et al. | 607/122 |
| 6,122,545 A | 9/2000 | Struble et al. | 607/9 |
| 6,496,730 B1 * | 12/2002 | Kleckner et al. | 607/9 |
| 6,574,506 B1 | 6/2003 | Kramer et al. | |

OTHER PUBLICATIONS

Guidant, "CONTAK TR CHFD Model 1241", *System Guide*, Congestive Heart Failure Device, (1999), 1-191.
Medtronic, "INSYNC III Device Model 8042", *Device Programming Guide*, INSYNC III Device Model 8042, Vision Programmer Software Model 9981, (2000), 1-260.
Medtronic, "INSYNC III Device Model 8042", *Device Reference Guide*, INSYNC III Device Model 8042, Vision Programmer Software Model 9981, (2002), 1-252.
St. Jude Medical, "Atlas + HF Models V-343, V-341", *User's Manual*, Implantable Cardioverter-Defibrillator, (Sep. 2003), 1-30.
St. Jude Medical, "Epic HF Model V-399", *User's Manual*, Implantable Cardioverter-Defibrillator, (Jul. 2002), 1-26.
St. Jude Medical, "Model 3510 Programmer with Model 3307 Software", *Reference Manual*, For Atlas, Atlas+, Epic, Epic+, Photon u and Photon Implantable Cardioverter/Defibrillators, (Sep. 2003), 1-314.

* cited by examiner

*Primary Examiner*—Kennedy Schaetzle
(74) *Attorney, Agent, or Firm*—Schwegman, Lundberg, Woessner, & Kluth, P.A.

(57) ABSTRACT

A device and method for cardiac rhythm management in which a heart chamber is paced in accordance with sense signals from the opposite chamber or other distant cardiac site. The method is particularly useful in delivering cardiac resynchronization therapy.

17 Claims, 6 Drawing Sheets

SYSTEM AND METHOD FOR TIMING SYNCHRONIZED PACING

CROSS REFERENCE TO RELATED APPLICATION(S)

This application is a continuation of U.S. patent application Ser. No. 09/748,736, filed on Dec. 26, 2000 now U.S. Pat. No. 6,574,506, the specification of which is incorporated herein by reference.

FIELD OF THE INVENTION

This invention pertains to methods and apparatus for cardiac rhythm management. In particular, the invention relates to methods and apparatus for providing cardiac resynchronization therapy.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects are also commonly found in CHF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

SUMMARY OF THE INVENTION

Cardiac resynchronization therapy can most conveniently be delivered by a cardiac rhythm management device in accordance with a bradycardia pacing mode so that the activation patterns between and within selected heart chambers are both resynchronized and paced concurrently. In accordance with the invention, one heart chamber, designated as the rate chamber, is paced with a bradycardia mode while the contralateral chamber or other pacing site, designated as the synchronized chamber or synchronized site, is paced with a synchronized pacing mode such that a pace is delivered at a specified pacing instant defined with respect to expiration of a rate chamber escape interval based upon rate chamber events. The rate chamber escape interval may be reset by a rate chamber sense or a pace to either chamber. This allows the rate at which the synchronized chamber is paced to be controlled only by intrinsic activity in the rate chamber. Because the synchronized chamber pace is not triggered by a rate chamber sense signal in this mode, the pacing instant for the synchronized chamber pace can be defined variably with respect to an accompanying rate chamber pace by a synchronized chamber offset interval. The synchronized chamber offset interval may be zero, positive, or negative so that the synchronized chamber is paced simultaneous with, after, or before the rate chamber is paced. The rate chamber may also be pseudo-paced such that the same timing is effected as with offset pacing, but only the synchronized chamber is paced. The use of a singe rate chamber for timing purposes not only facilitates the desired resynchronization of the synchronized chamber, but also allows the use of common timing and timing markers across multiple cardiac rhythm management therapies, such as tachycardia and bradycardia pacing.

DESCRIPTION OF THE INVENTION

Figure 1:
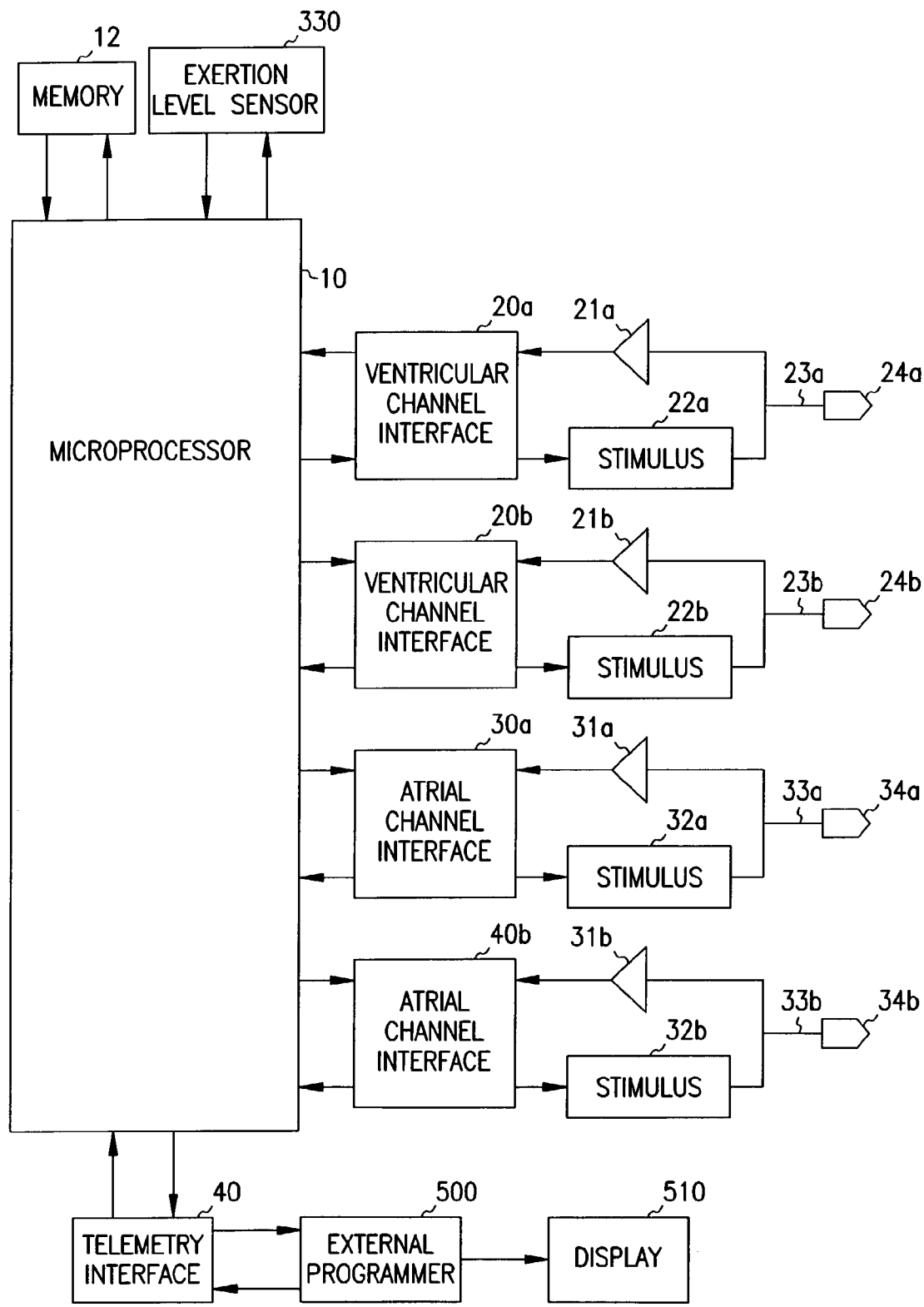
FIG. 1 is a system diagram of a pacemaker configured for biventricular pacing and sensing.

When one heart chamber is paced and the contralateral chamber is not paced, the paced chamber contracts earlier than the opposite chamber, which creates an uncoordinated bilateral contraction sequence that deteriorates heart pumping function. To help prevent this deterioration, devices have been made to pace both right and left chambers simultaneously. Such devices employ the normal pacemaker bradycardia pacing modes to set the rate of simultaneous right and left ventricular paced pulses. One such mode is a synchronous pacing mode, which inhibits and reschedules pacing when an intrinsic depolarization is sensed at the pacing site prior to pacing that site.

For some applications, including resynchronization of bilateral contraction sequence, it may be advantageous to pace with short delays between right and left pacing pulses, with either the right or left chamber being paced first. Problems arise when the right and left chambers are to be paced non-simultaneously with a synchronous bradycardia mode, because intrinsic depolarizations sensed in either chamber will inhibit and reset pacing in both chambers. For example, the pacing rate will vary depending on whether a sense occurred first in the right chamber or the left chamber. Also it may be important to deliver a pace to one chamber even though a sense occurred in the opposite chamber. In accordance with the present invention, right and left chambers are paced non-simultaneously with pacing rate based on sensing from only one of the bilateral chambers, designated the rate chamber, and pacing of the opposite chamber, designated the synchronized chamber, is synchronized by an offset interval to the rate chamber pacing. For example, a synchronous mode pacing rate will be determined only by the rate chamber sensing, and pacing can occur in the rate chamber even when an intrinsic depolarization is sensed first in the opposite chamber. Also in accordance with the present invention, while basing the pacing rate on sensing from only one of the bilateral chambers, it is possible also to pace either chamber after a short delay following sensing of an intrinsic depolarization in the contralateral chamber. This provision extends the flexibility to pace one chamber even after a sense in the opposite chamber. All these provisions pertain more generally to a multisite pacing device that provides for multiple pacing sites within one or more paired heart chambers wherein intrinsic depolarizations sensed from only one site is used to set the pacing rate. All other pacing sites are paced synchronized by offset intervals to the pacing at the site having rate sensing.

A problem that arises when a pacing instant for a synchronized heart chamber or other synchronized site is based upon whether or not a sense signal is received only from the contralateral rate chamber (or distant rate site within the same chamber as the synchronized site) is that the risk of a pace being delivered near the time of a prior contraction and during a vulnerable period is increased. This is because the pacing of a synchronized site is then neither inhibited nor triggered by intrinsic activity at that site, which activity may occur sooner or later than that of the rate site during a particular cardiac cycle. In accordance with the present invention, a protection period begins after the sensing of intrinsic activity at the synchronized site to be paced. The protection period then prevents any pacing from being delivered to the synchronized site for the duration of the period. Pacing of the synchronized site is then inhibited in a manner that does not otherwise disturb the pacing algorithm.

1. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, implements timers for defining escape intervals and sensory refractory periods, and performs the pace counting functions as described below. It should be appreciated, however, that these functions could also be performed by custom logic circuitry either in addition to or instead of a programmed microprocessor.

2. Bradycardia Pacing Modes

Bradycardia pacing modes refer to pacing algorithms used to pace the atria and/or ventricles when the intrinsic atrial and/or ventricular rate is inadequate due to, for example, sinus node dysfunction or AV conduction blocks. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which intrinsic atrial rates are unreliable or pathological. In a rate-adaptive pacemaker, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

Other therapeutic alterations of cardiac function through multisite pacing changes in activation and contraction sequences are included in the meaning of cardiac resynchronization therapy. For instance, pacing at more than one site within a heart chamber to desynchronize the contraction sequence of that chamber may be therapeutic in patients with hypertrophic obstructive cardiomyopathy, where creating asynchronous contractions with multi-site pacing reduces the abnormal hyper-contractile function of the chamber. Similarly altering bilateral contraction sequences or intrachamber contraction sequences by pre-exciting one site relative to another site may be used to alter the regional workload and metabolic energy demand of the pre-excited region in order to allow regions of damaged heart tissue to recover from injury or disease.

It is advantageous to deliver resynchronization therapy in conjunction with one or more synchronous bradycardia pacing modes, such as are described above. One atrial and/or one ventricular sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber in accordance with a synchronized pacing mode as described below.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

FIGS. 2–8 illustrate some of the specific synchronized pacing modes to be described below. A timeline is shown for each channel, with the channels designated as RC for rate chamber, SC for synchronized chamber, ARC for atrial rate chamber, ASC for atrial synchronized chamber, VRC for ventricular rate chamber, and VSC for ventricular synchronized chamber. In each channel, paces are designated as P, inhibited paces are designated as P*, pseudo-paces are designated as P+, and senses are designated as S.

Figure 2:
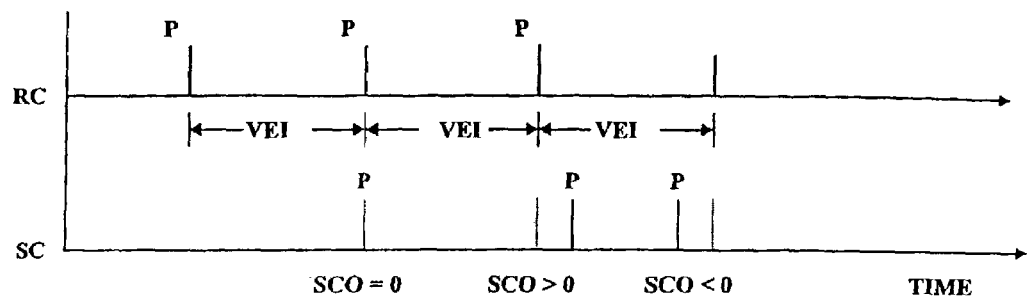
FIGS. 2 through 8 illustrate timing diagrams of different synchronized pacing modes.

FIG. 2 is an example of single-chamber bradycardia pacing with resynchronization, illustrating zero, positive, and negative synchronized chamber offset intervals (SCO). The VEI is defined as the interval between the rate chamber paced events while the SCO is defined as an offset of the synchronized chamber (SC) pace from the rate chamber (RC) pace. Negative and positive offset intervals between 0–120 ms may benefit some patients with severe left or right bundle branch conduction delays and heart dilatation.

Figure 3:
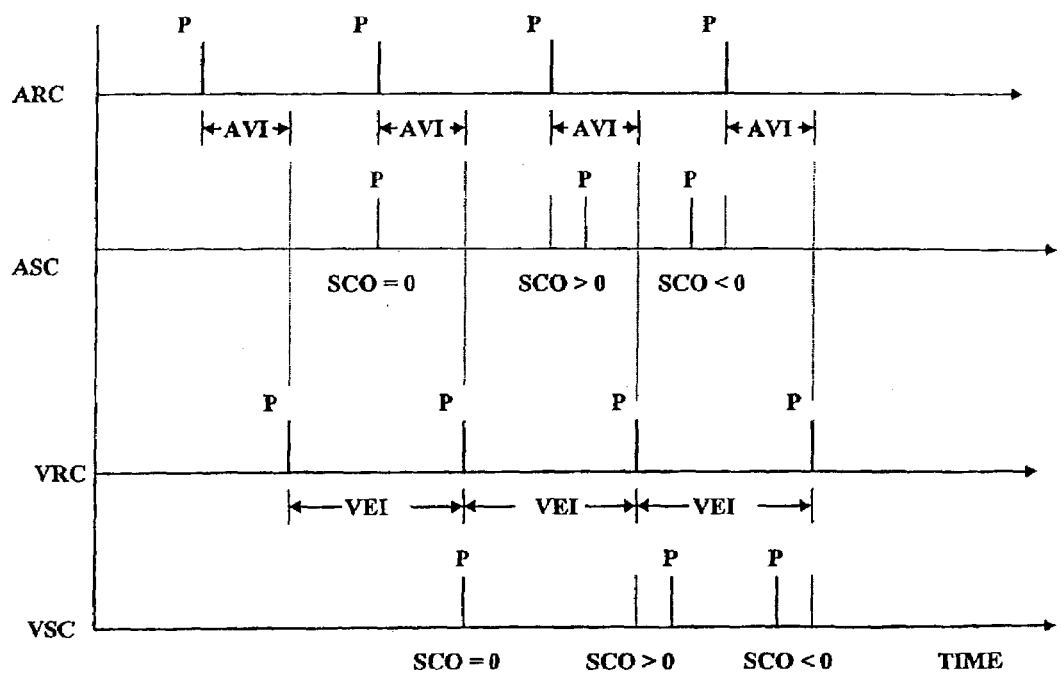
Figure 4:
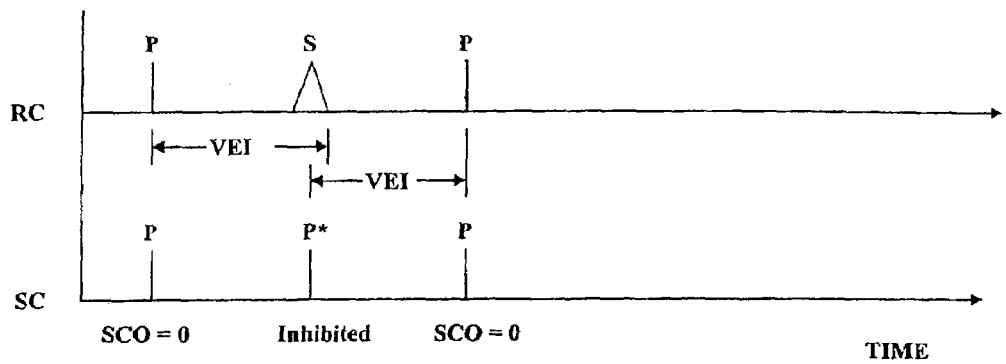

FIG. 3 is an example of dual-chamber bradycardia pacing with resynchronization and various SCOs. The VEI is defined in this case as the interval between the ventricular rate chamber paced events and the AVI is defined as the interval between the atrial and ventricular rate chamber paced events. The SCO for the atrium is defined as an offset of the atrial synchronized chamber and rate chamber paces and the SCO for the ventricle is defined as an offset of the ventricular synchronized chamber and rate chamber paces. The atrial and ventricular SCOs can be independently programmed. FIG. 4 is another illustration of the offset synchronized pacing mode in which the second synchronized chamber pace is inhibited by the rate chamber sense. The rate chamber sense resets the VEI of the rate chamber and the next scheduled synchronized chamber pace.

In the preferred embodiment, pacing in the paired rate and synchronized chambers cannot be inhibited or reset during the SCO interval. Thus, if SCO>0, then after the rate chamber pace occurs, the synchronized chamber pace is committed to occur after the SCO interval. Conversely, if SCO<0, then after the synchronized chamber pace occurs, the rate chamber pace is committed to occur after the SCO interval. Committed SCO pacing can be implemented by controller logic that ignores any sensing events detected in either paired chamber during the SCO interval (i.e., a concurrent sensing refractory period), or the SCO interval can be associated with a concurrent sensing blanking period, during which time sensing in either paired chamber is disabled.

Figure 5A:
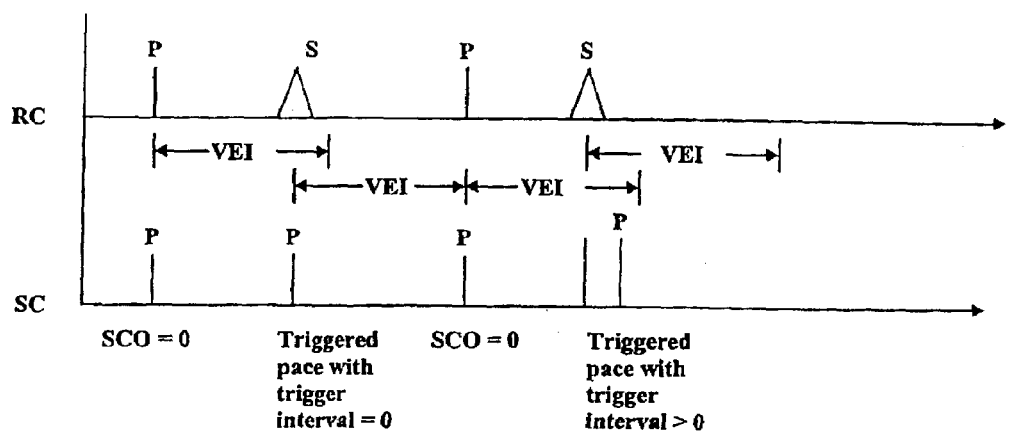
Figure 5B:
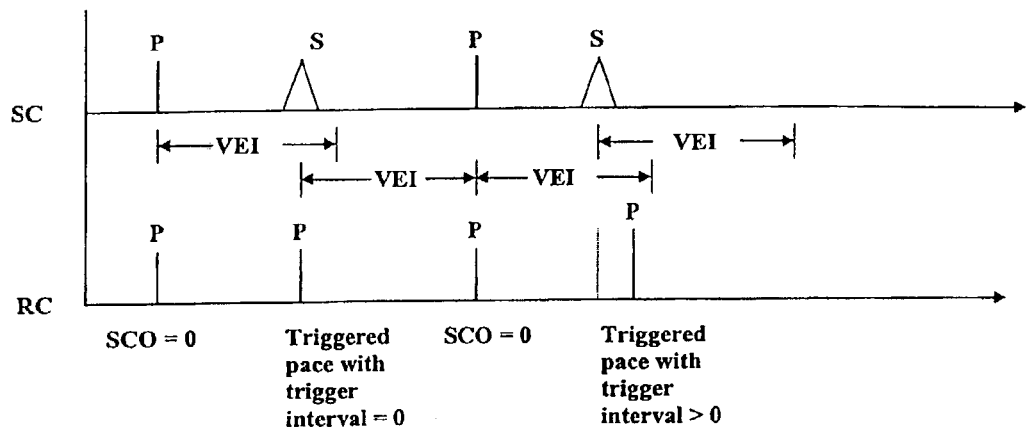

Another resynchronization mode is triggered synchronized pacing. In one type of triggered synchronized pacing, the synchronized chamber is paced after a specified trigger interval following a sense in the rate chamber, as illustrated in FIG. 5A with a trigger interval of zero at the first RC sense and a non-zero trigger interval at the second RC sense. In another type, the rate chamber is paced after a specified trigger interval following a sense in the synchronized chamber as illustrated in FIG. 5B, with a trigger interval of zero at the first SC sense and a non-zero trigger interval at the second SC sense. The two types may also be employed simultaneously. For example, with a trigger interval of zero, pacing of one chamber is triggered to occur in the shortest time possible after a sense in the other chamber in order produce a coordinated contraction. (The shortest possible time for the triggered pace is limited by a sense-to-pace latency period dictated by the hardware.) The triggered synchronized pacing mode may be desirable when an abnormal intra-chamber conduction time is long enough that the pacemaker is able to reliably insert a pace before depolarization from one chamber reaches the other. In another case, it may be desirable to delay triggered pacing of the synchronized chamber with a non-zero trigger interval to mimic the normal physiological conduction delay between the two chambers. For example, when the left atrium pacing is triggered by a sensed depolarization in the right atrium, a non-zero trigger interval can reproduce a physiologically appropriate interatrial conduction delay.

Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of the mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

Figure 6:
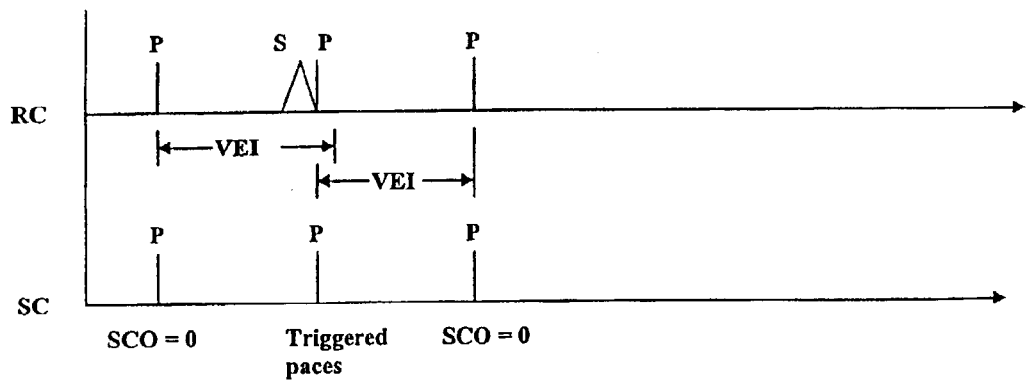
Figure 7:
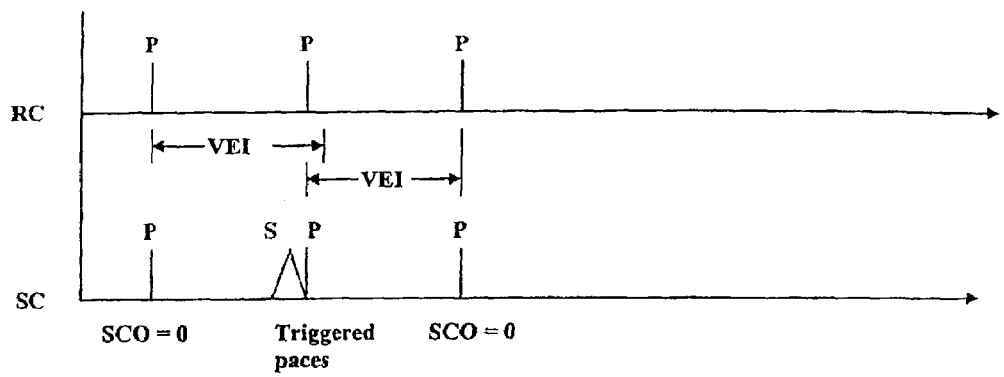

In a variation of the type of triggered synchronized pacing in which the rate chamber is paced after a trigger interval following a sense in the synchronized chamber, a pace is also triggered immediately to the synchronized chamber, such as is illustrated in FIG. 7. The advantage of this is that the sensed event in the synchronized chamber sensing channel might actually be a far-field sense from the rate chamber, in which case the synchronized chamber should be paced to coordinate with the rate chamber depolarization. If the synchronized chamber sense were actually from that chamber, the synchronized chamber pace would occur during that chamber's physiological refractory period and cause no harm. Similarly, in a triggered synchronized pacing mode in which the synchronized chamber is paced after a trigger interval following a sense in the rate chamber, a pace may be also triggered immediately to the rate chamber as illustrated in FIG. 6. One way of implementing this mode is to control the rate chamber by a triggered bradycardia mode so that a sense in the rate chamber sensing channel, in addition to triggering a pace to the synchronized chamber, also triggers an immediate rate chamber pace and resets any rate chamber escape interval. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pace the synchronized chamber and pseudo-pace the rate chamber immediately before expiration of any rate chamber escape intervals, where a pseudo-pace is a zero energy or virtual pace used to trigger or terminate timing events within the pacemaker. The pseudo-pace thus inhibits a rate chamber pace and resets any rate chamber escape intervals. Such pseudo-pacing can be combined with the offset synchronized pacing mode using a negative offset to pace the synchronized chamber and simultaneously pseudo-pace the rate chamber before expiration of the rate chamber escape interval. The result is that only the synchronized chamber is paced. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

Figure 8A:
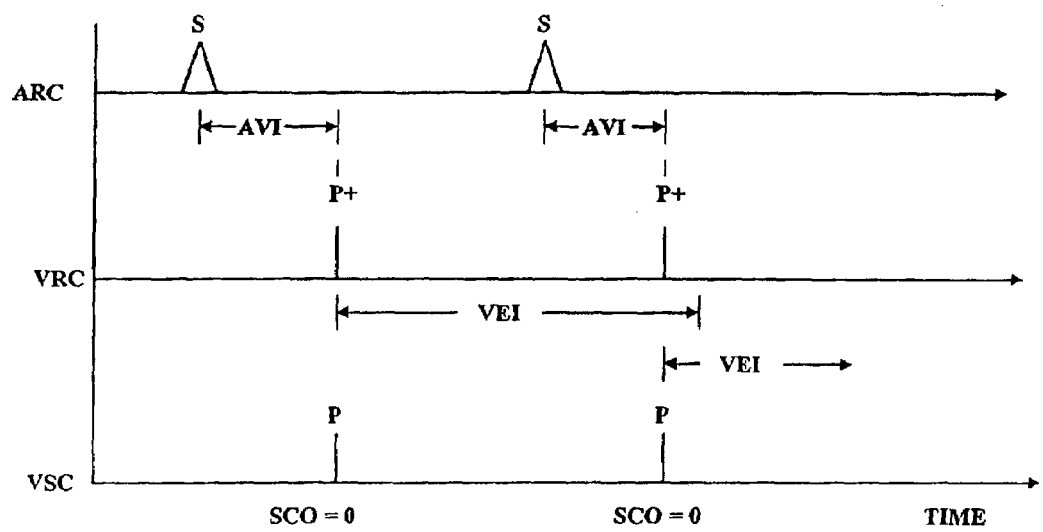
Figure 8B:
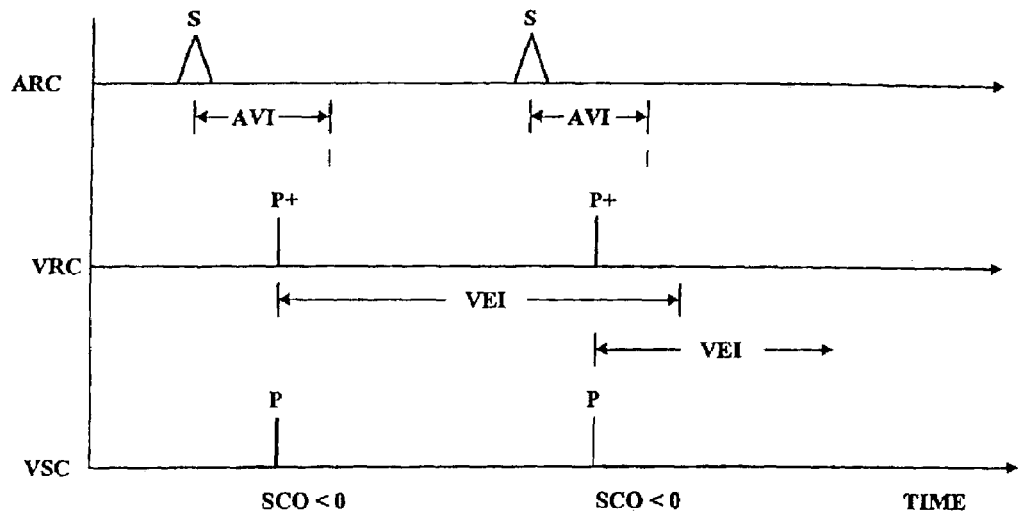
Figure 8C:
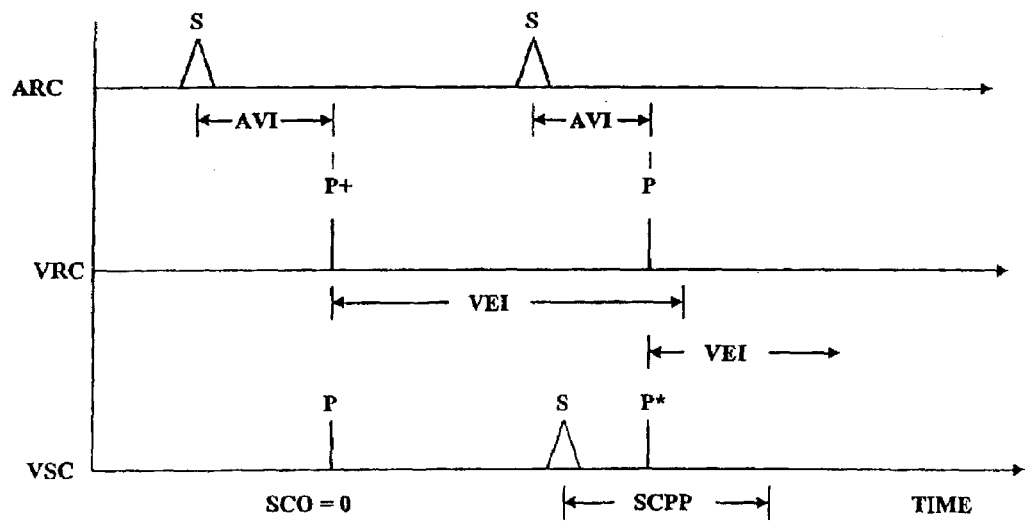

Synchronized chamber-only pacing is illustrated in FIGS. 8A–C for a dual chamber pacing mode. In FIG. 8A, an atrial rate chamber (ARC) sense triggers an AVI, at the end of which a ventricular rate chamber (VRC) pace would be delivered, but which is inhibited by the ventricular synchronized chamber (VSC) pace at zero synchronized chamber offset (SCO) and simultaneous VRC pseudo-pace. FIG. 8B is similar, but illustrates timing with SCO<0. In FIG. 8C, an SC sense occurs, initiating a synchronized chamber protection period (SCPP, described below) that inhibits the second scheduled VSC pace, which in turn allows the VRC pace to occur in the same cycle. With SCO>0, the rate chamber is paced first so the synchronized chamber pace does not reset rate chamber pacing. One clinical use of synchronized chamber-only pacing is to synchronize paced pre-excitation of the synchronized chamber with intrinsic activation of the rate chamber. This will be most effective with a dual-chamber pacing mode, where the synchronized chamber is a ventricle delayed by bundle branch block and the paired ventricular rate chamber is normally activated by intrinsic atrio-ventricular conduction. Then the AVI and SCO are set as in the examples of FIGS. 8A–C to pace the ventricular synchronized chamber so that paced and intrinsic activation of the ventricles combine in a beneficial way.

In the resynchronization modes described above, the rate chamber is synchronously paced with a mode based upon detected intrinsic activity in the rate chamber, thus protecting the rate chamber against paces being delivered during the vulnerable period. In order to provide similar protection to the synchronized chamber, a synchronized chamber protection period (SCPP) may be provided. The SCPP is a programmed interval which is initiated by a sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only pacing, a synchronized chamber pace may be inhibited if a synchronized chamber sense occurs within a protection period prior to expiration of the rate chamber escape interval or synchronized chamber offset interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

Synchronized pacing may be applied to multiple sites of a single chamber. In these resynchronization modes, one sensing/pacing channel is designated as the rate channel for sensing/pacing a rate site, and the other sensing/pacing channels in either the same or the contralateral chamber are designated as synchronized channels for sensing one or more synchronized sites. Pacing and sensing in the rate channel follows rate chamber timing rules, while pacing and sensing in the synchronized channels follows synchronized chamber timing rules as described above. The same or different synchronized pacing modes may be used in each synchronized channel.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:
   sensing a site in a heart chamber designated as a rate site and generating a rate site sense upon detection of depolarization occurring at the rate site;
   pacing another site in the same heart chamber designated as a synchronized site at a pacing instant defined with respect to expiration of an escape interval; and,
   restarting the escape interval only after a rate site sense or after a synchronized site pace.

2. The method of claim 1 further comprising sensing the synchronized site and wherein the escape interval is not restarted after a synchronized site sense.

3. The method of claim 1 wherein the heart chamber is a ventricle.

4. The method of claim 1 wherein the heart chamber is an atrium.

5. The method of claim 1 wherein the pacing instant for the synchronized site is coincident with expiration of the escape interval.

6. The method of claim 1 further comprising pacing one or more additional synchronized pacing sites at pacing instants defined with respect to expiration of the escape interval.

7. The method of claim 1 wherein the synchronized site is paced at a pacing instant defined with respect to expiration of the escape interval by an offset interval.

8. The method of claim 1 further comprising pacing the rate site upon expiration of the escape interval.

9. A cardiac rhythm management device, comprising:
   means for sensing a site in a heart chamber designated as a rate site and generating a rate site sense upon detection of depolarization occurring at the rate site;
   means for pacing another site in the same heart chamber designated as a synchronized site at a pacing instant defined with respect to expiration of an escape interval; and,
   means for restarting the escape interval only after a rate site sense or a synchronized site pace.

10. The device of claim 9 further comprising means for sensing the synchronized site and wherein the escape interval is not restarted after a synchronized site sense.

11. The device of claim 9 wherein the heart chamber is a ventricle.

12. The device of claim 9 wherein the heart chamber is an atrium.

13. The device of claim 9 wherein the pacing instant for the synchronized site is coincident with expiration of the escape interval.

14. The device of claim 9 further comprising means for pacing one or more additional synchronized pacing sites at pacing instants defined with respect to expiration of the escape interval.

15. The device of claim 9 wherein the synchronized site is paced at a pacing instant defined with respect to expiration of the escape interval by an offset interval.

16. The device of claim 9 further comprising means for pacing the rate site upon expiration of the escape interval.

17. The device of claim 9 further comprising means for pacing the synchronized site at a specified trigger interval after a rate site sense.

* * * * *

UNITED STATES PATENT AND TRADEMARK OFFICE
CERTIFICATE OF CORRECTION

PATENT NO. : 7,158,828 B2 Page 1 of 1
APPLICATION NO. : 10/454014
DATED : January 2, 2007
INVENTOR(S) : Kramer et al.

It is certified that error appears in the above-identified patent and that said Letters Patent is hereby corrected as shown below:

On the face page, in Item (56), under "Other Publications", in column 2, line 11, delete "V-399" and insert -- V-339 --, therefor.

Signed and Sealed this

Seventeenth Day of April, 2007

JON W. DUDAS
*Director of the United States Patent and Trademark Office*